United States Patent
Maheshwari et al.

(10) Patent No.: US 6,812,363 B2
(45) Date of Patent: Nov. 2, 2004

(54) RACEMIZATION OF OPTICALLY ACTIVE 2-SUBSTITUTED PHENYL GLYCINE ESTERS

(75) Inventors: Krishna K. Maheshwari, Mumbai (IN); Rayaprolu Kodandarama Sarma, Mumbai (IN); Shreerang Vidyadhar Joshi, Mumbai (IN); Anup Ramkrishna Barde, Mumbai (IN); Rajiv Pandurang Sutar, Maharashtra (IN); Prasad Vasudeo Ranade, Maharashtra (IN)

(73) Assignee: USV Limited, Mumbai (IN)

( * ) Notice: Subject to any disclaimer, the term of this patent is extended or adjusted under 35 U.S.C. 154(b) by 121 days.

(21) Appl. No.: 10/271,299

(22) Filed: Oct. 15, 2002

(65) Prior Publication Data

US 2004/0073057 A1 Apr. 15, 2004

(51) Int. Cl.$^7$ ............................................. C07C 229/00
(52) U.S. Cl. ....................................................... 560/38
(58) Field of Search ........................................... 560/38

(56) References Cited

U.S. PATENT DOCUMENTS

| 4,237,313 A | 12/1980 | Higo et al. |
| 4,529,596 A | 7/1985 | Aubert et al. |
| 4,647,692 A | 3/1987 | Jacewicz |
| 4,713,470 A | 12/1987 | Mirviss |
| 4,847,265 A | 7/1989 | Badorc et al. |
| 5,204,469 A | 4/1993 | Descamps et al. |
| 6,040,482 A | 3/2000 | Harris et al. |
| 6,180,793 B1 | 1/2001 | Bakonyi et al. |

FOREIGN PATENT DOCUMENTS

| WO | WO 98/39286 | * 9/1998 |

* cited by examiner

Primary Examiner—Rita Desai
Assistant Examiner—Hector M. Reyes
(74) Attorney, Agent, or Firm—GIbbons, Del Deo, Dolan, Griffinger & Vecchione

(57) ABSTRACT

A process for preparing racemic mixtures containing nearly equal amounts of stereo isomers of compounds of formula (I), or their salts, by heating an enantiomerically enriched material with thionyl chloride.

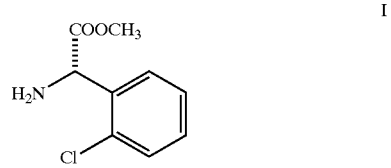

A required useful enantiomer may thereby be recovered from unwanted mother liquors that would otherwise be otherwise be discarded.

6 Claims, No Drawings

RACEMIZATION OF OPTICALLY ACTIVE 2-SUBSTITUTED PHENYL GLYCINE ESTERS

BACKGROUND TO THE INVENTION

1. Field of the Invention

The present invention pertains to a process for the recovery of enantiomers from unwanted mother liquors using racemic mixtures containing stereoisomers having the structure (I) below, or its salt, by heating an enantiomerically enriched chemical mixture with thionyl chloride.

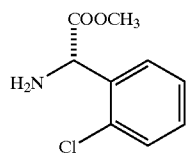

I

The present invention is also directed to a process for preparing racemic mixtures containing nearly equal amounts of enantiomers of 2-chlorophenyl glycine methyl ester from mother liquors enriched with unwanted isomers, as its hydrochloride salt, by heating the mother liquors with thionyl chloride.

2. Discussion of Related Art

Racemization is generally carried out by heating an acid with or without the presence of an alkali or a solvent. Free amino acids are difficult to racemize. The temperature required for racemization is often in the range of 140°–180° C. and some decomposition occurs at temperatures within this high range.

Decomposition is extensive with 2-(2-chlorophenyl) glycine, not only because it is difficult to racemize, but also because it easily degrades. 2-(2-chlorophenyl) glycine is an intermediate required in its enantiomerically pure (S) enantiomer for the production of methyl alpha-5 (4,5,6,7-tetrahydro (3,2,-c) thienopyridyl) (2-chlorophenyl)-acetate) to produce an important active pharmaceutical ingredient known as clopidogrel. The enantiomerically pure form of 2-(2-chlorophenyl) glycine is derived from its racemic mixture by optical resolution separation techniques.

The fact that single isomer chiral molecules are known to racemize and revert to optically inactive racemic molecules under adverse conditions is well known in the art. *Chemistry and Biochemistry of the Amino Acids*, edited by G. C. Barret Chapman and Hall, Chapter Thirteen, deals in some detail with the subject of racemization of amino acids.

U.S. Pat. No. 4,713,470 (the "'470 patent") describes racemization of amino acids carried out by using specially prepared polymers. The racemization process described in the '470 patent uses an aromatic aldehyde polymer synthesized by reacting an hydroxylaromatic aldehyde with a chloromethylated vinylbenzene polymer under reactive conditions to form an aromatic aldehyde polymer wherein the aldehydic moiety is linked to the polymer through an ether linkage. There is also disclosed a process for the production of the racemization catalyst used therein.

U.S. Pat. No. 4,647,692 (the "'692 patent") is directed to a process for racemization of amino acids by using ketones and organic acids such as acetic acid. Specifically, the '692 patent discusses a process for resolution of free α-amino acids with in situ racemization. The resolution of 4-hydroxyphenylglycine and 3,4-dihydroxy-phenylglycine with 3-bromocamphor-9-sulphonic acid with in situ racemization is specifically mentioned.

U.S. Pat. No. 4,638,086 (the "086 patent") covers a process for racemization of optically active amino acids that comprises heating amino acids with an effective amount of benzoic or phenylacetic acid or their derivatives which are monosubstituted or polysubstituted on the nucleus by identical or different substituents selected from the group consisting of halogen, lower alkyl, lower alkoxy, hydroxy, acyloxy, and nitro.

U.S. Pat. No 4,237,313 (the "'313 patent") is directed to a process for the racemization of optically active phenylacetic acid derivatives. The process comprises heating an optically active phenylacetic acid derivative to a temperature of at least 150° C. in the presence or absence of an inert solvent. None of the above-referenced patents teach a process for the recovery of a racemate of a compound represented by the general structure (I) below from unwanted mother liquors that are rich in one of the enantiomers thereof;

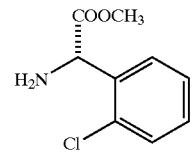

I

Compounds obtained by reacting esters of 2-chlorophenylglycine with thienopyridine are useful in the treatment of cardiac conditions and may also be used as anti-platelet agents. U.S. Pat. No. 4,847,265 refers to the (S)+enantiomer of clopidogrel. Other patents such as U.S. Pat. Nos. 4,529,596 and 5,204,469, also refer to methylalpha-5(4,5,6,7-tetrahydro(3,2-c)thienopyridyl)(2-chlorophenyl)-acetate, its isomers and its methods of preparation. U.S. Pat. No. 6,180,793 refers to this compound and also to methods of preparing the required intermediates. These patents refer to the chemical synthesis of racemic (S)(+) or (R)(−) clopidogrel by various methods. In some instances, the resulting clopidogrel is resolved in the end, while in other instances, the resolution step is carried during an intermediate stage.

In each of the aforementioned patents mentioned in the above paragraph, half of the material produced is typically discarded as the unwanted isomer. It may be either in one of the intermediate stages or in the final stage of clopidogrel. For example, the '793 patent covers synthesis of clopidogrel wherein the resolution step is carried out in any of four different stages in the progression of the synthesis. In any of these steps, the unwanted isomer, representing approximately 50% of the quantity produced, is discarded. Discarding of this material is expensive and contributes to total production cost. It also forms an effluent and increases effluent treatment costs. From an economic viewpoint, it is wasteful to discard an otherwise useful enantiomer from an enantiomerically enriched mixture, such as mother liquors with unwanted isomers. It is preferable to convert these mother liquors into the desired enantiomers via racemization techniques followed by separation of the desired isomer using optical resolution, thereby recovering the required enantiomer from what would otherwise be wasted material.

SUMMARY OF THE INVENTION

One aspect of the present invention pertains to a process for the recovery of enantiomers from racemic mixtures containing stereoisomers of compounds having the general formula (I) below

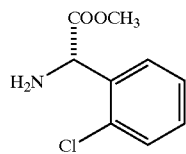

or its salt by heating an enantiomerically enriched chemical mixture with thionyl chloride.

Another aspect of the present invention includes:
a. Liberating 2-chlorophenyl glycine methyl ester as free base from a concentrated (R)-enantiomer enriched mother liquor, which contains the tartarate or D-camphorsulfonate salt of an unwanted enantiomer;
b. Heating the free base with thionyl chloride so as to effect racemization to form racemized ester hydrochloride;
c. Isolating the racemized ester hydrochloride; and
d. Liberating a racemized ester from the isolated, racemized ester hydrochloride as a further free base from its hydrochloride salt.

The racemized ester may be further processed by conventional resolution steps well known in the art. The present invention thus offers the advantage of recovering a desired enantiomer from unwanted mother liquors that would be otherwise discarded. It further provides an environmental advantage in that chemical waste is reduced.

DETAILED DESCRIPTION OF THE INVENTION

The present invention relates to a racemization process for re-use of 2-(2-chlorophenyl) glycine from an enantiomerically enriched mixture. The methyl ester of racemic 2-(2-chlorophenyl) glycine is resolved using either D-camphor sulfonic acid or tartaric acid. Generally tartaric acid or D-camphorsulfonic acid is added to a solution of 2-chlorophenylglycine in a suitable solvent such as methanol. On cooling, the required enantiomer precipitates out as a D-camphor sulfonate salt or as a tartarate salt.

The mother liquor contains the solvent and the D-camphor sulfonate or tartarate salt of the 2-(2-chlorophenyl) glycine methyl ester. According to the process covered by the present invention it can be further processed. The mother liquor is first concentrated by removing the solvent under reduced pressure. The concentrated mother liquor of tartarate generally exhibits an optical rotation $[\alpha]_D^{20}$ between $-85°$ and $+5°$, C=1 in methanol.

The concentrated liquors are then treated with an alkali, preferably sodium hydroxide to liberate the 2-(2-chlorophenyl) glycine methyl ester as its base.

The base solution obtained from the above-step is dissolved in approximately ten times the volume of methanol. An equimolar amount of thionyl chloride is added to this solution and the mixture is heated between 30° C. and 90° C. for a period ranging between 2 hrs to 20 hrs, preferably 8 to 12 hrs. At the end of this period, the specific optical rotation of the resulting mixture is nearly zero which indicates successful racemization.

The racemized solution contains the 2-(2-chlorophenyl) glycine methyl ester as the hydrochloride. This solution is treated with an alkali preferably sodium hydroxide solution to liberate the racemized ester. This material is now ready for processing into clopidogrel following any of the techniques described in the patents referred to previously.

It should be appreciated that this process allows for the recovery and recyclability of a substantial portion of the starting material in the synthesis of clopidogrel. This result provides substantial monetary savings and reduces environmental waste.

While the following examples specifically describe this process, the invention should not be limited by what is described below but only by the claims.

The following examples further describe the present invention.

EXAMPLE 1

Liberation of free (−) enriched 2-(2-chlorophenyl) glycine methyl ester free base from its tartaric acid salt:

To (−) enriched methyl 2-(2-chlorophenyl) glycinate(+) tartaric acid salt of methyl 2-chlorophenyl glycinate, 90 Kg present in 30 liters methanol, 450 liters of 10% sodium bicarbonate solution (45 Kg of sodium bicarbonate dissolved in 450 lits of water) is added slowly while stirring keeping the temperature of the reaction mixture between 25° C.–30° C., until a pH of the solution is in the range of 7.0–7.5 (checked by means of pH meter.) Thereafter, stirring is discontinued and the reaction mixture is allowed to settle. The bottom layer of methyl 2-(2-chlorophenyl) glycinate is separated and fifty liters of dichloromethane is charged for the extraction of the upper aqueous layer. The reaction mixture is stirred for 15 minutes, and then the layers are allowed to separate. The lower dichloromethane extract is removed and combined with the methyl 2-(2-chlorophenyl) glycinate layer. This mixture is dried over anhydrous sodium sulfate (5 Kg) and dichloromethane distilled at atmospheric pressure.

Yield: −45 to 50 Kg.

Specific Optical Rotation (SOR)(hydrochloride)$[\alpha]_D^{20}$ −85° to 5° (c=1% in methanol)

EXAMPLE 2

Racemization of methyl 2-chlorophenyl glycinate and isolation of liberated racemized ester as free base.

One hundred kilograms of methyl 2-(2-chlorophenyl) glycinate (SOR −85° to +5°) is dissolved in three hundred fifty liters (350 liters) of methanol in a 1000 liter Mild Steel glass lined reactor. This mixture is cooled to 5° C. by circulating chilled water or brine through an external jacket.

Forty five liters (73.7 kilograms) of thionyl chloride are added to the reaction mixture while stirring and maintaining a temperature of the reaction mixture between 25° C. and 30° C. After completion of the addition, water or brine circulation is stopped and heating of the reaction mixture begins by means of hot water circulation through an external jacket. Heating is continued and reflux is maintained for about twelve hours.

The methanol is now slowly distilled out while maintaining reduced pressure so as to maintain the temperature of the reaction mixture below 60° C. Distillation is continued until three hundred liters of methanol is distilled out. The reaction mixture is then cooled to 25° C.–30° C. and five hundred liters (500 liters) of water is added to the reaction mixture while stirring. Stirring is continued until a clear solution is obtained. The reaction mixture is then cooled to 10° C. 47% caustic lye is added slowly, while maintaining stirring, until a pH between 7.0 and 7.5 of the reaction mixture is obtained.

Stirring and cooling are then stopped and the reaction mixture is allowed to settle. The organic layer is separated as (±)-methyl-2-(2-chlorophenyl) glycinate.

Yield: ~75–80 kilograms

SOR(hydrochloride) $[\alpha]_D^{20} = -5$ to $+5°$ ($c = 1\%$ in methanol)

The racemized ester solution is now ready for resolution as per methods available in prior art. In an analogous manner, the unwanted enantiomers of 2-(2-bromophenyl)-glycine and 2-(2-methoxyphenyl)glycine may also be racemized and recovered.

EXAMPLE 3

Conversion of methyl 2-(2-chlorophenyl) glycinate to its tartaric acid salt.

60 kilograms of (+) tartaric acid (SOR=12° c=20, $H_2O$) is dissolved in three hundred fifty liters of methanol in a mild steel glass lined reactor. Methyl 2-(2-chlorophenyl) glycinate obtained by the previous procedure (eighty kilograms) is dissolved in fifty liters of methanol and added to the reaction mixture at once. The reaction mixture is stirred for approximately five minutes and transferred to a high density polyethylene tank. Five grams of pure tartaric acid salt of methyl 2-(2-chlorophenyl) glycinate(SOR=~90°) is added as seed. The reaction mass is kept at room temperature for ninety six hours.

Crystals of (+) tartaric acid salt of methyl-2-(2-chlorophenyl) glycinate and separated by centrifugation and dried at 40° C. for eight hours.

Yield: ~49–50 kilograms

Specific optical rotation $[\alpha]_D^{20} = 85°$ –93° ($c = 1\%$ in methanol)

EXAMPLE 4

Isolation of Second Crop:

The mother liquor of example 3 is transferred to a reactor and the methanol is distilled out under reduced pressure while maintaining the temperature below 60° C. After recovery of approximately 250 liters of methanol, the reaction mass is collected in polyethylene drums and allowed to solidify. The solid mass containing hemitartarate of (–)-methyl 2-(2-chlorophenyl) glycinate as a major product is stored as second crop for future reprocessing. Yield: About 100–120 kg.

SOR after drying at 60° C. $[\alpha]_D^{20} = -85°$ to $+5°$ ($c = 1\%$ in methanol)

EXAMPLE 5

Isolation of methyl-2-(2-chlorophenyl) glycinate from second crop generated after resolution.

The second crop obtained after resolution (SOR=–85° to +5° degrees) is dissolved in 700 liters of water. 40% caustic lye is added until a pH between 7.0–7.5. is obtained. Once the pH range is attained, stirring is stopped and the reaction mass is allowed to settle. A lower layer of methyl 2-chlorophenyl glycinate is separated and 50 liters of dichloromethane is added to the reactor and stirred for 15 minutes. A lower dichloromethane layer is separated and combined with the product and dried over anhydrous sodium sulphate.

Dichloromethane is then recovered under reduced pressure keeping the temperature within the range 25° C.–30° C. degrees.

Yield: 40–45 Kg. (SOR as HCl=–85° to +5°; c=1% in methanol)

Methyl-2-(2-chlorophenyl) glycinate obtained by above procedure is racemized, resolved and converted to (+) methyl-2-(2-chlorophenyl) glycinate as per examples 1 and 2.

EXAMPLE 6

Isolation of Resolved Ester from Tartarate

The (+)-methyl-2-(2-chlorophenyl) glycinate (+)tartaric acid salt of methyl-2-(2-chlorophenyl) glycinate obtained in Example-3 above (fifty kilograms) is dissolved in two hundred liters (200 liters) of water in a clean stainless steel reactor. 10% sodium bicarbonate solution is added while stirring keeping the temperature of the reaction mixture between 25° C.–30° C., until a pH of the solution is within the range of 7.0–7.5 (checked by means of pH meter.) Upon attaining the preferred pH stirring is stopped and the reaction mixture is allowed to settle. A layer of methyl-2-(2-chlorophenyl) glycinate is separated and fifty liters of dichloromethane is charged for the extraction of the upper aqueous layer. This is stirred for 15 minutes and then stopped allowing the layers to separate. The lower dichloromethane extract layer is separated and combined with (+)-methyl-2-(2-chlorophenyl) glycinate. This mixture is dried over anhydrous sodium sulfate (5 Kg) and dichloromethane recovered under vacuum keeping the temperature between 25–30° C.

Yield: ~27.5 Kg.

SOR(hydrochloride) $[\alpha]_D^{20} = +114$ to $+115°$ ($c = 1\%$ in methanol)

What is claimed is:

1. A process for preparing a racemate of a compound represented by structure (I):

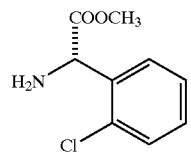

from a mixture that is rich in an enantiomer of said compound, said process comprising treating said mixture with thionyl chloride to form said racemate; and recovering said racemate therefrom.

2. A process in accordance with claim 1, wherein said treatment with thionyl chloride comprising adding thionyl chloride to said enriched enantiomer mixture and heating at a temperature of from about 30° C. to about 90° C.

3. A process in accordance with claim 2, wherein said mixture is a mother liquor enriched in said one enantiomer, said process including the steps of concentrating the mother liquor, treating the concentrated mother liquor with alkali and dissolving the resulting mixture in an excess of methanol prior to treatment with thionyl chloride.

4. A process in accordance with claim 3, wherein the methanol solution is cooled to a temperature of about 5° C. prior to the treatment with thionyl chloride and maintained at a temperature of from about 25° C. to about 30° C. during the addition of thionyl chloride.

5. A process in accordance with claim 3, wherein the step of recovering the racemate comprises removing the methanol from said solution by distilling at a temperature below about 60° C.; cooling the residue; mixing said residue with sufficient water to obtain at clear solution; adding sufficient caustic to the resulting solution to obtain a pH of between 7.0 and 7.5 thereby causing said racemate to separate, as an organic layer; and recovering the resulting organic layer containing the racemate.

6. A process in accordance with claim 3, wherein said solution formed by the addition of water is cooled to about 10° C. prior to the addition of the caustic.

* * * * *